United States Patent [19]
Hoenig et al.

[11] Patent Number: 5,702,396
[45] Date of Patent: Dec. 30, 1997

[54] OSTEOSYNTHESIS PLATE

[76] Inventors: Johannes Franz Hoenig, Nikolausbergerweg 3 A, 37073 Goettingen, Germany; Kevin Thomas Stone, 2940 E. Patterson Rd., Warsaw, Ind. 46580

[21] Appl. No.: 688,737
[22] Filed: Jul. 31, 1996

Related U.S. Application Data

[63] Continuation of Ser. No. 622,162, Mar. 27, 1996.

[30] Foreign Application Priority Data

Mar. 27, 1995 [DE] Germany .................. 195 11 268.7

[51] Int. Cl.⁶ ................................................ A61B 17/58
[52] U.S. Cl. ................................................ 606/69; 606/70
[58] Field of Search .................. 606/69, 70, 71, 606/60, 75, 76, 77

[56] References Cited

U.S. PATENT DOCUMENTS

| | | |
|---|---|---|
| 3,463,148 | 8/1969 | Treace . |
| 4,263,904 | 4/1981 | Judet . |
| 4,429,690 | 2/1984 | Angelino-Pievani . |
| 4,683,878 | 8/1987 | Carter . |
| 5,006,120 | 4/1991 | Carter . |
| 5,041,114 | 8/1991 | Chapman et al. . |
| 5,084,050 | 1/1992 | Draenert ............... 606/77 |
| 5,151,103 | 9/1992 | Tepic et al. ............ 606/69 |
| 5,246,458 | 9/1993 | Graham ................. 606/60 |
| 5,269,784 | 12/1993 | Mast . |
| 5,474,553 | 12/1995 | Baumgart ............. 606/71 |

FOREIGN PATENT DOCUMENTS

| | | | |
|---|---|---|---|
| 3743638 | 7/1989 | Germany ............. 606/69 |
| 1502020 | 8/1989 | U.S.S.R. ............. 606/69 |

*Primary Examiner*—Michael Buiz
*Assistant Examiner*—Julian W. Woo
*Attorney, Agent, or Firm*—Wigman, Cohen, Leitner & Myers, P.C.

[57] ABSTRACT

An osteosynthesis plate. An osteosynthesis plate is disclosed having a regular knob profile, preferably a spherical knob profile, whereby the knob height, measured between the deepest profile point and the peak of the knobs, is between a selected optimal range of heights, and the distance between successive knobs, measured between the highest points of two successive knobs, is between a selected optimal range of distances.

7 Claims, 1 Drawing Sheet

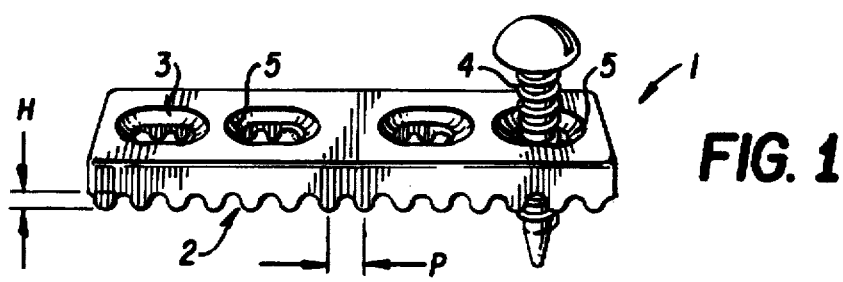
FIG. 1
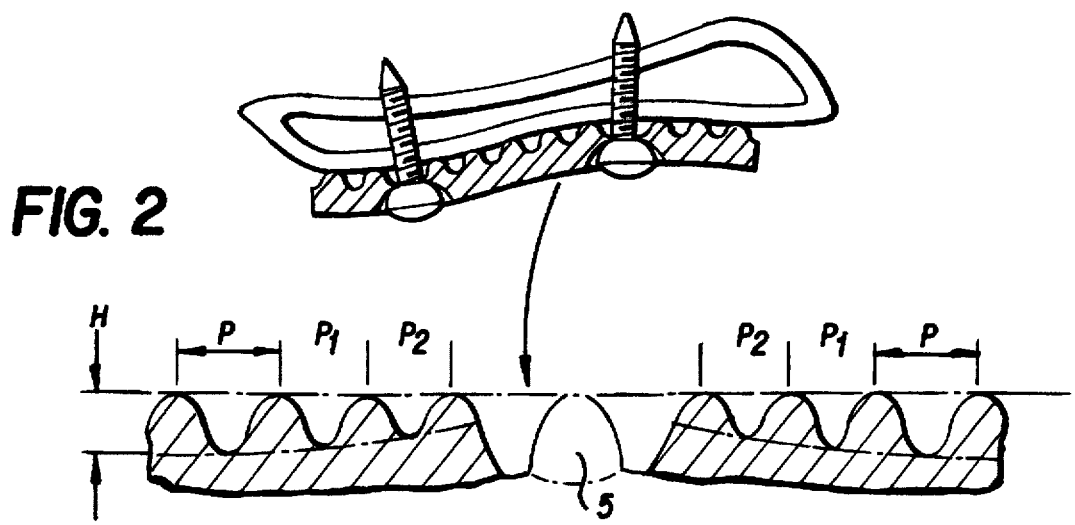
FIG. 2
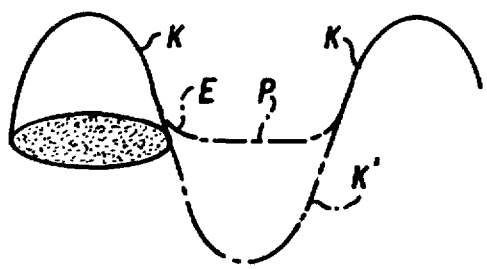
FIG. 3
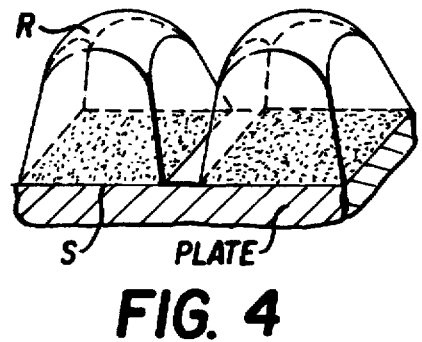
FIG. 4
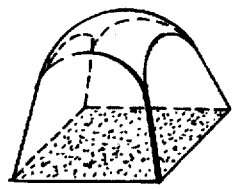
FIG. 6
FIG. 5

OSTEOSYNTHESIS PLATE

RELATED APPLICATION

This application is a continuation of Ser. No. 08/622,162, filed Mar. 27, 1996 INC'D May 9, 1996.

FIELD OF THE INVENTION

This invention relates to an osteosynthesis plate which is used for anatomical reduction of bone fragments after fractures, for stabilization of bone fragments in surgical treatment of craniofacial anomalies, malocclusions and reconstructions after tumor resections, etc.

BACKGROUND OF THE INVENTION

German patent no. 37 43 638 discloses such an osteosynthesis plate whereby its surfaces facing the bone is structured, being designed in particular with spherical knobs. Such a knob profile is basically very well-suited for fixing the bone fragments in stable fashion, without a deficient supply of the periosteum and necrosis of the bone tissue occurring at the contact points.

The problem underlying the invention is to modify this known osteosynthesis plate and to state parameters which permit optimal fixation of the bone fragments without impairing the supply of the periosteum and the bone tissue.

SUMMARY OF THE INVENTION

This problem is solved according to the invention in that the knob profile is of substantially regular and in particular spherical design in a section along successive knobs, the height of the knobs being between about 0.4 and 2.5 millimeters, measured between the deepest and highest points, i.e. between knob valley and knob peak, and the period of successive knobs being between 0.8 and 3.5 millimeters, measured as the distance between the peaks of two successive knobs.

For the knob height one preferably maintains values between 0.5 and 1.5 millimeters, and for the knob period values between 1.5 and 2.5 millimeters.

To obtain essentially equal strength properties over the entire contact surface of the osteosynthesis plate, the height and the period of the knobs can be of precisely variable design; in particular one will make the knob height and/or knob period smaller in the area of screw holes than in the remaining area.

An osteosynthesis plate with the stated dimensions stabilizes the bone fragments in the desired position; the multiple point-shaped contain results in a good pressure distribution over the entire osteosynthesis plate. With this osteosynthesis plate the bone tissue can grow into the spaces between the knobs, resulting in a mechanical attachment so that the fixation is produced not only by friction but also by form closure. When it is positioned on the periosteum the tissue is additionally preserved and an unimpaired arteriovenous circulation permitted under the plate (in the area of the knob spaces).

BRIEF DESCRIPTION OF THE DRAWING

The invention will be explained more closely in an embodiment example with reference to the drawing, in which:

FIG. 1 shows a schematic perspective plan view of an osteosynthesis plate according to the invention;

FIG. 2 shows a longitudinal section through an osteosynthesis plate according to FIG. 1 which is fastened to a bone fragment.

FIGS. 3 to 6 show different forms of knobs of an osteosynthesis plate according to the invention.

DETAILED DESCRIPTION OF THE INVENTION

FIG. 1 shows a perspective view of elongate rectangular osteosynthesis plate 1. The upper side of the osteosynthesis plate is smooth while the underside shows a knob profile. This knob profile is a spherical profile, whereby the profile course in a section in the longitudinal direction of the plate is composed of alternately concave or convex aligned semicircles. FIG. 1 shows "period" P of the knob profile, i.e. the distance between the peaks of two successive knobs. This period is between 1.0 and 3.5 millimeters, preferably between 1.0 and 2.5 millimeters, and on the average about 1.0 to 1.2 millimeters. Knob height H, i.e. the distance between a knob valley and a knob peak, is between 0.4 and 2.5 millimeters, preferably between 0.8 and 1.2 millimeters.

In the longitudinal direction the plate has a plurality of screw holes 3 in the center in which fixing screws 4 can be screwed for fixing the bone fragments to the osteosynthesis plate, as shown in FIG. 2. Screw holes 3 have on both or at least one of their sides ramps 5 extending in the longitudinal direction of the osteosynthesis plate; the heads of the screws have a crowned conical design. Such a design permits the osteosynthesis plate to be shifted forcibly in the longitudinal direction when the head of screw 4 is screwed in, thereby e.g. pushing a bone fragment toward the fracture fissure. This reduces the size of the fracture fissure, thereby furthering the healing process.

As shown shaded in FIG. 2, the knob dimensions can be reduced in the area of the screws, i.e. the period and the height are made smaller than on the remaining underside of the osteosynthesis plate. This permits uniform strength properties to be achieved over the entire surface of the osteosynthesis plate.

As is clear from FIG. 2, the osteosynthesis plate according to the invention can be adapted well with the knob profile to the macrostructure of a bone. The knobs, which in the favorable case engage into the depth of the macrorelief of the bone, lead to increased retention between the plate and the ends of fractured bone and thus to improved stabilization of the fracture planes. The risk of pseudarthroses, wound-healing impairments or even necroses can thus be practically excluded.

FIG. 3 shows knobs and a part of the knob profile along a section of the osteosynthesis plate. The knobs K each have a circular base C and a somewhat sinusoidal profile. The bottom of the knob profile may be formed by "negative" knobs K' as described above or by a more or less plain bottom P so that the knobs protrude from this bottom. They may be separated from each other by a certain distance as shown in the figure or they are in a more or less direct contact to each other. Because of strength properties the egdes between the knobs and the bottom P may be rounded as indicated by E.

FIG. 4 shows two knobs having the form of a frustum of a pyramid with a rectangular or square base S. The upper edges of the frustum are rounded as indicated by R. The knobs of the profile are in direct contact to each other or may be arranged as shown in FIG. 3, that is either neighbored or surrounded by similar "negative" knobs or by "plane" areas.

The knob according to FIG. 5 is a frustum of a pyramid having a triangular base T. The upper edges may be rounded and the arrangement of the knobs may be similar to FIGS. 3 or 4.

The knob of FIG. 6 is similar to FIG. 4, but the top of the knob has the form of a sphere which verges smoothly into the side walls of the pyramid. The arrangement of the knobs is similar to FIGS. 3 or 4.

The dimensions of the knobs shown in FIGS. 3 to 6 are in the range as described above with respect to FIGS. 1 and 2.

We claim:

1. An osteosynthesis plate for anatomical reduction of bone fragments after fractures and osteotomies, for stabilization of bone fragments in surgical treatment of craniofacial anomalies, malocclusions and reconstructions after tumor resections, comprising a surface of the osteosynthesis plate facing the bone having a knob profile comprising a plurality of knobs, each having a height and each separated by a distance, the height of the knobs in the knob profile, in a section along successive knobs, is between 0.4 and 2.5 millimeters, measured between the deepest profile point and the peak of the knobs, and the distance between successive knobs is between 0.8 and 3.5 millimeters, measured between the highest points of two successive knobs, wherein the height of the knobs and the distance between the highest points of the knobs are of precisely variable design so that essentially equal strength properties are maintained over the entire plate surface, and wherein the knob dimensions including the height of the knobs and the distance between the highest points of two adjacent knobs, are designed smaller in the area of screw holes than in the remaining surface area.

2. An osteosynthesis plate for anatomical reduction of bone fragments after fractures and osteotomies, for stabilization of bone fragments in surgical treatment of craniofacial anomalies, malocclusions and reconstructions after tumor resections, comprising a surface of the osteosynthesis plate facing the bone having a knob profile comprising a plurality of knobs, each having a height and each separated by a distance, the height of the knobs in the knob profile, in a section along successive knobs, is between 0.4 and 2.5 millimeters, measured between the deepest profile point and the peak of the knobs, and the distance between successive knobs is between 0.8 and 3.5 millimeters, measured between the highest points of two successive knobs, wherein each knob has the form of a truncated cone.

3. The osteosynthesis plate of claim 2, wherein the upper surface of the truncated form is rounded.

4. An osteosynthesis plate for anatomical reduction of bone fragments after fractures and osteotomies, for stabilization of bone fragments in surgical treatment of craniofacial anomalies, malocclusions and reconstructions after tumor resections, comprising a surface of the osteosynthesis plate facing the bone having a knob profile comprising a plurality of knobs, each having a height and each separated by a distance, the height of the knobs in the knob profile, in a section along successive knobs, is between 0.4 and 2.5 millimeters, measured between the deepest profile point and the peak of the knobs, and the distance between successive knobs is between 0.8 and 3.5 millimeters, measured between the highest points of two successive knobs, wherein each knob has the form of a frustum of a pyramid.

5. The osteosynthesis plate of claim 4, wherein the upper edges of the frustum are rounded.

6. The osteosynthesis plate of claim 4, wherein the upper surface of the knob has the form of a sphere which verges smoothly into the side walls of the pyramid.

7. The osteosynthesis plate of claim 4, wherein the base of the pyramid is rectangular or triangular.

* * * * *